US009431731B2

(12) United States Patent
Oba et al.

(10) Patent No.: US 9,431,731 B2
(45) Date of Patent: Aug. 30, 2016

(54) SENSOR AND TERMINAL MEMBER

(71) Applicant: NGK SPARK PLUG CO., LTD., Nagoya-shi, Aichi (JP)

(72) Inventors: Takehiro Oba, Konan (JP); Yuichi Yamada, Komaki (JP); Shingo Ito, Ichinomiya (JP); Takeshi Nanbu, Aichi (JP); Hironari Furuta, Tajima (JP); Makoto Kume, Inuyama (JP)

(73) Assignee: NGK SPARK PLUG CO., LTD., Aichi (JP)

( * ) Notice: Subject to any disclaimer, the term of this patent is extended or adjusted under 35 U.S.C. 154(b) by 214 days.

(21) Appl. No.: 14/246,336

(22) Filed: Apr. 7, 2014

(65) Prior Publication Data
US 2014/0298931 A1 Oct. 9, 2014

(30) Foreign Application Priority Data

Apr. 8, 2013 (JP) .................... 2013-080275

(51) Int. Cl.
*H01R 11/18* (2006.01)
*H01R 11/01* (2006.01)
*G01N 27/406* (2006.01)
*H01R 13/24* (2006.01)

(52) U.S. Cl.
CPC ............ *H01R 11/18* (2013.01); *G01N 27/4062* (2013.01); *H01R 11/01* (2013.01); *H01R 13/2442* (2013.01)

(58) Field of Classification Search
CPC ....... H01R 11/18; H01R 11/01; H01R 11/22; G01N 27/4062
See application file for complete search history.

(56) References Cited

U.S. PATENT DOCUMENTS 6,231,348 B1    5/2001    Mayer et al.
2009/0101503 A1*   4/2009   Kanao ................ G01N 27/4062
                                                                                                                       204/424

FOREIGN PATENT DOCUMENTS

JP    2000-500876 A    1/2000
JP    2005-91223 A    4/2005

* cited by examiner

*Primary Examiner* — Paul West
(74) *Attorney, Agent, or Firm* — Sughrue Mion, PLLC

(57) ABSTRACT

A sensor includes a detection element; a plurality of terminal members, each of the terminal members including an elongated frame body portion extending along the axial direction, an element contact portion in elastic contact with an electrode terminal, and a folded portion connecting the frame body portion and the element contact portion; and a separator. The element contact portion of each of the terminal members has a turning portion which turns inward with respect to the width direction between the folded portion and a contact portion in contact with an electrode terminal. In those two of the terminal members which are adjacent to each other along the width direction, the distance along the width direction between the contact portions is smaller than the distance along the width direction between the frame body portions.

7 Claims, 12 Drawing Sheets

SENSOR AND TERMINAL MEMBER

This application is based on Japanese Patent Application No. 2013-080275, filed Apr. 8, 2013, incorporated herein by reference in its entirety.

TECHNICAL FIELD

The present invention relates to a sensor and terminal members for use in the sensor.

BACKGROUND ART

A conventionally known sensor has a plate-like detection element extending in the axial direction (refer to, for example, Patent Documents 1 and 2). The detection element has a plurality of electrode terminals formed on its rear end portion for outputting detection signals to an external device therefrom. The plurality of electrode terminals are disposed on at least one of a first main surface and a second main surface of the detection element. Such a sensor is used as a gas sensor, such as a full range air/fuel ratio sensor, an oxygen sensor, or an $NO_x$ sensor, or as a temperature sensor for detecting temperature.

Such a sensor has current paths electrically connected to the plurality of electrode terminals for outputting detection signals to an external device. A plurality of terminal members corresponding to the plurality of electrode terminals are used to partially constitute the electrode paths. The plurality of terminal members are in elastic contact with the corresponding electrode terminals, thereby being electrically connected to the corresponding electrode terminals.

PRIOR ART DOCUMENTS

[Patent Document 1] Japanese Patent Application Laid-Open (kokai) No. 2005-091223

[Patent Document 2] Japanese Kohyo (PCT) Patent Publication No. 2000-500876

SUMMARY OF THE INVENTION

Problems to be Solved by the Invention

In recent years, the detection element has been reduced in size for the purpose of, for example, reduction of cost and sensor size. For example, as the width of the detection element becomes narrower, spacings between the plurality of electrode terminals disposed on the main surface(s) of the detection element become narrower. Therefore, there has been desired a technique for electrically insulating the plurality of terminal members from one another while establishing good contact between the terminal members and the corresponding electrode terminals. The width of the detection element is a dimension of the detection element measured along a direction orthogonal to the axial direction and in parallel with the first main surface.

Means for Solving the Problems

The present invention has been conceived to solve the above problems and can be embodied in the following modes or application examples.

(1) A mode of the present invention provides a sensor comprising a plate-like detection element extending along an axial direction and having a first main surface and a second main surface which face opposite each other and constitute a portion of a surface of the detection element, a first side surface and a second side surface which face opposite each other, extend along the axial direction, and constitute a portion of the surface of the detection element, and a plurality of electrode terminals disposed on at least one of the first and second main surfaces; a plurality of terminal members provided in correspondence with the plurality of electrode terminals and electrically connected to the corresponding electrode terminals, each of the terminal members comprising an elongated frame body portion extending along the axial direction, an element contact portion in elastic contact with the corresponding electrode terminal, and a folded portion connecting the frame body portion and the element contact portion; and a separator surrounding the element contact portions and that portion of the detection element at which the plurality of electrode terminals are disposed.

In this sensor, with a direction in which the first main surface and the second main surface face opposite each other being defined as a thickness direction of the detection element, and a direction in which the first side surface and the second side surface face opposite each other being defined as a width direction of the detection element, two or more of the plurality of electrode terminals are disposed along the width direction; the element contact portion of each of the plurality of terminal members has a contact portion in contact with the corresponding electrode terminal, and a turning portion which turns inward with respect to the width direction between the folded portion and the contact portion; and in those two of the plurality of terminal members which are adjacent to each other along the width direction, a distance along the width direction between the contact portions is smaller than a distance along the width direction between the frame body portions.

According to the sensor of this mode, by means of the terminal members having the turning portions, while spacing is provided between the frame body portions of two terminal members adjacent to each other along the width direction, good contact can be established between the element contact portions of the terminal members and the corresponding electrode terminals of the detection element.

(2) The sensor of the above-mentioned mode may be such that an electrically insulating partition wall is disposed between the frame body portions of the two terminal members which are adjacent to each other along the width direction.

According to the sensor of this mode, by means of the electrically insulating partition wall being disposed between the adjacent frame body portions, there can be reduced the possibility of electrical connection between the adjacent frame body portions. Thus, the detection accuracy of the sensor can be improved.

(3) The sensor of either one of the above-mentioned modes may be such that, of side surfaces of the frame body portion, an inner side surface located inward with respect to the width direction is located outward of the detection element with respect to the width direction.

According to the sensor of this mode, sufficient spacing can be provided between the frame body portions which are adjacent to each other with respect to the width direction.

(4) The sensor of any one of the above-mentioned modes may be such that a width of the contact portion is narrower than a width of the folded portion.

According to the sensor of this mode, while deterioration in rigidity of the folded portion is restrained, elastic force (contact pressure) which the contact portion applies to the electrode terminal can be increased.

(5) The sensor of any one of the above-mentioned modes may be such that: two of a plurality of the frame body portions constitute a pair of the frame body portions disposed in a facing manner on opposite sides of the detection element with respect to the thickness direction; an electrically insulating side partition wall is disposed between the paired frame body portions and faces the first side surface of the detection element; and the side partition wall is located inward, with respect to the width direction, of those outer side surfaces of the paired frame body portions which are located outward with respect to the width direction.

According to the sensor of this mode, by means of the side partition wall being located inward of the outer side surfaces of the paired frame body portions with respect to the width direction, spacing along the width direction between the side partition wall and the detection element can be reduced. Thus, even when the detection element receives a force in the width direction due to vibration of the sensor, or the like, the side partition wall can restrict movement of the detection element along the width direction. Therefore, positional misalignment of the detection element within the sensor can be restrained.

(6) Another mode of the present invention provides a terminal member which is brought into electrical contact with an electrode terminal provided on a detection element extending along an axial direction. The terminal member comprises an elongated frame body portion extending along the axial direction; an element contact portion which comes into elastic contact with the electrode terminal and which faces, at least partially, the frame body portion with respect to a thickness direction orthogonal to the axial direction; and a folded portion connecting the frame body portion and the element contact portion; wherein, with a direction orthogonal to the axial direction and to the thickness direction being defined as a width direction of the terminal member, the element contact portion has a contact portion which comes into contact with the electrode terminal, and a turning portion which turns toward the width direction between the folded portion and the contact portion.

The terminal member of this mode has the turning portion which turns toward the width direction; thus, even when a plurality of the terminal members are attached to the sensor in such a manner as to be adjacent to one another in the width direction, while spacing is provided between frame body portions adjacent to each other along the width direction, good contact can be established between the element contact portions of the terminal members and the corresponding electrode terminals of the detection element. That is, by means of use of two adjacent terminal members whose turning portions turn toward opposite directions along the width direction, while spacing is provided between the frame body portions adjacent to each other along the width direction, good contact can be established between the element contact portions of the terminal members and the corresponding electrode terminals of the detection element.

(7) The terminal member of the above-mentioned mode may be such that a width of the contact portion is narrower than a width of the folded portion.

According to the sensor of this mode, while deterioration in rigidity of the folded portion is restrained, elastic force (contact pressure) which the contact portion applies to the electrode terminal can be increased.

The present invention can be embodied in various forms other than a sensor and a terminal member. For example, the invention can be embodied in a method of manufacturing a sensor and a method of manufacturing a terminal member.

MODES FOR CARRYING OUT THE INVENTION

A. First Embodiment

A-1. Configuration of Sensor

Figure 1:
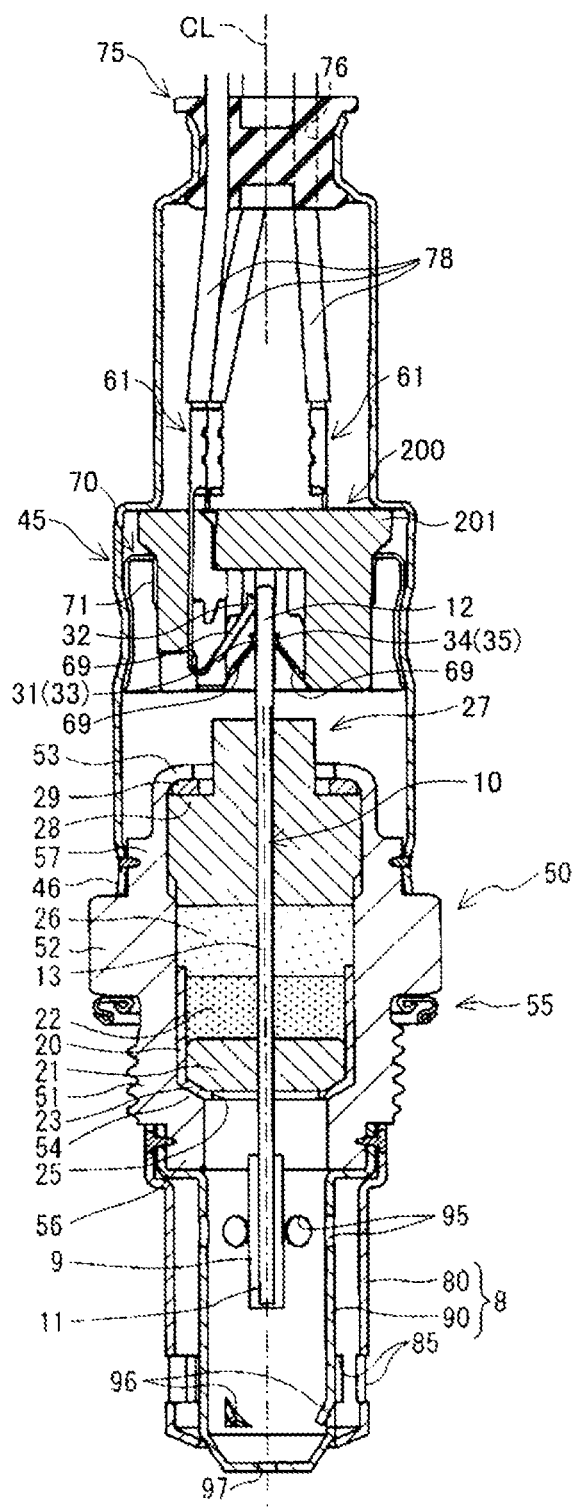
FIG. 1 Sectional view of a gas sensor according to a first embodiment of the present invention.

FIG. 1 is a sectional view of a gas sensor 1 according to a first embodiment of the present invention. In FIG. 1, an axial direction CL of the gas sensor 1 corresponds to the vertical direction. In the following description, a side toward a forward end portion 11 of a detection element 10 held in the interior of the gas sensor 1 is referred to as a forward side CL1 of the gas sensor 1, and a side toward a rear end portion 12 is referred to as a rear side CL2 of the gas sensor 1.

The gas sensor 1 shown in FIG. 1 is attached to an exhaust pipe (not shown) of an automobile. The gas sensor 1 is attached such that the forward end portion 11 of the detection element 10 held therein is exposed to exhaust gas which flows through the exhaust pipe. By means of exposure of the forward end portion 11 to exhaust gas, the gas sensor 1 detects the air/fuel ratio of exhaust gas on the basis of oxygen concentration in the exhaust gas. That is, the gas sensor 1 is a so-called full range air/fuel ratio sensor.

The detection element 10 assumes a plate-like form extending along the axial direction CL. The left-right direction on paper on which FIG. 1 appears corresponds to the thickness direction of the detection element 10, and the far side-near side direction with respect to paper on which FIG. 1 appears corresponds to the width direction of the detection element 10. The gas sensor 1 has a structure in which the detection element 10 is held in a metallic shell 50 used for attachment to an exhaust gas (not shown) of an automobile, by holding the detection element 10 in a cup 20 and supporting the cup 20 in the metallic shell 50.

The cup 20 is formed of metal and assumes a closed-bottomed tubular form. The cup 20 is a holding member for holding the detection element 10 in the metallic shell 50, and the detection element 10 is held while extending through an opening 25 formed in the bottom of the cup 20. The forward end portion 11 of the detection element 10 protrudes from the opening 25 toward the forward side CL1. The forward end portion 11 functions as a detection portion for detecting an oxygen gas component in exhaust gas. A detection portion protection layer 9 covers the outer surface of the forward end portion 11 for protecting the forward end portion 11 from poisoning by exhaust gas.

A forward-end peripheral portion 23 is a peripheral portion of the bottom of the cup 20 and is tapered. The cup 20 accommodates a ceramic ring 21 made of alumina and a talc ring 22 formed through compression of talc powder such that the detection element 10 extends through the ceramic ring 21 and the talc ring 22. The talc ring 22 is accommodated in the cup 20 in a crushed condition. In this manner, the detection element 10 is positioned and held in the cup 20.

The detection element 10 united with the cup 20 is held while being surrounded by the tubular metallic shell 50. The metallic shell 50 is formed of low-carbon steel such as SUS430. The metallic shell 50 has an externally threaded portion 51 formed on its outer circumference at a position located toward the forward end and used for attachment to an exhaust pipe. The metallic shell 50 has a forward-end engagement portion 56 which is formed on the forward side CL1 with respect to the externally threaded portion 51 and with which a protector S to be described later is engaged. The metallic shell 50 has a tool engagement portion 52 which is formed at a central portion with respect to the axial direction CL and with which an attaching tool is engaged. A gasket 55 is fitted to the metallic shell 50 between the forward end surface of the tool engagement portion 52 and the rear end of the externally threaded portion 51 for preventing gas leakage after attachment to the exhaust pipe. The metallic shell 50 has a rear-end engagement portion 57 which is formed on the rear side with respect to the tool engagement portion 52 and with which a tubular housing 45 to be described later is engaged, as well as a crimped portion 53 which is formed on the rear side with respect to the rear-end engagement portion 57 and holds the detection element 10 in the metallic shell 50 through crimping.

The metallic shell 50 has a stepped portion 54 formed on the inner circumference at a position substantially corresponding to the externally threaded portion 51. The forward-end peripheral portion 23 of the cup 20 is seated on the stepped portion 54. Furthermore, a talc ring 26 is inserted into the metallic shell 50 from the rear side of the cup 20 with the detection element 10 extending therethrough and is disposed in an accommodating space defined by the cup 20 and the metallic shell 50. A tubular sleeve 27 is fitted into the metallic shell 50 in such a manner as to press the talc ring 26 from the rear side. The sleeve 27 has a shoulder portion 28 formed in a stepped form on the outer circumference at a position located toward its rear end. An annular crimp packing 29 is disposed on the shoulder portion 28. In this condition, the crimped portion 53 of the metallic shell 50 is crimped so as to press forward the shoulder portion 28 of the sleeve 27 through the crimp packing 29. The talc ring 26 is crushed in the metallic shell 50 by the sleeve 27, thereby filling the accommodating space. By means of the talc ring 26 and the talc ring 22, which is charged beforehand, the cup 20 and the detection element 10 are positioned and held in the metallic shell 50.

The forward end portion 11 of the detection element 10 protrudes toward the forward side CL1 from the forward end (forward-end engagement portion 56) of the metallic shell 50. The protector 8 is attached to the forward-end engagement portion 56. The protector 8 protects the forward end portion 11 of the detection element 10 from fouling of deposits (poisoning substances such as fuel ash and oil) contained in exhaust gas, breakage caused by adhesion of water contained in exhaust gas, etc. The protector 8 has a dual structure consisting of an inner protector 90 which assumes a closed-bottomed tubular form and has inner introduction holes 95, and a tubular outer protector 80 which radially surrounds the inner protector 90 with a gap formed between the same and the outer circumferential surface of the inner protector 90 and has outer introduction holes 85.

Exhaust gas introduced from the outer introduction holes 85 into the gap between the outer protector 80 and the inner protector 90 swirls around the outer circumference of the inner protector 90 and is separated into gas and water. The gas is introduced into the inner protector 90 from the inner introduction holes 95, comes into contact with the detection element 10, and is then discharged from a discharge hole 97 to the outside. Meanwhile, water enters the inner protector 90 from drain holes 96 and is then discharged from the discharge hole 97 to the outside. By virtue of such constitution, the forward end portion 11 of the detection element 10 is protected from fouling of deposits contained in exhaust gas, breakage caused by thermal shock stemming from adhesion of water, etc.

Meanwhile, the rear end portion 12 of the detection element 10 protrudes toward the rear side CL2 from the rear end (crimped portion 53) of the metallic shell 50. Five electrode terminals 31 to 35 (see FIG. 2) formed of platinum (Pt) are formed on the rear end portion 12 of the detection element 10 for outward connection. Terminal members 61 are provided in correspondence with electrode terminals 31 to 35 and are in elastic contact with the electrode terminals 31 to 35, respectively. More specifically, element contact portions 69 of the terminal members 61 are in elastic contact with the corresponding electrode terminals 31 to 35. Five terminal members 61 are provided in correspondence with the five electrode terminals 31 to 35 (FIG. 1 shows only two of them). As will be described later, the present embodiment uses three types of the terminal members 61 which differ in shape. When a distinction between the three types of the terminal members 61 is required, the terms "first-type terminal member 61A," "second-type terminal member 61B," and "third-type terminal member 61C" are used. They may be called merely "terminal member 61A," "terminal member 61B," and "terminal member 61C." Also, the element contact portion 69 may be called as follows: the element contact portion of the first-type terminal member 61A may be called "element contact portion 69A;" the element contact portion of the second-type terminal member 61B may be called "element contact portion 69B;" and the element contact portion of the third-type terminal member 61C may be called "element contact portion 69C."

The gas sensor 1 further includes a tubular separator 200. The separator 200 is formed of electrically insulating ceramic. The separator 200 surrounds the rear end portion 12 of the detection element 10 and the element contact portions 69. That is, the separator 200 is disposed radially outward of the rear end portion 12 and the element contact portions 69.

The separator 200 accommodates, for protection, connections between the terminal members 61 and five lead wires 78 (FIG. 1 shows three of them) extending outward from the gas sensor 1. The five terminal members 61 are disposed between the detection element 10 and the separator 200. The five terminal members 61 are electrically connected, at their rear ends, to the five lead wires 78, respectively. This connection establishes current paths for current which flows between the electrode terminals 31 to 35 and external apparatus to which the lead wires 78 are connected.

The tubular housing 45 is attached to the rear side of the metallic shell 50. The tubular housing 45 is formed by forming stainless steel (e.g., SUS304) into a tubular shape. The tubular housing 45 surrounds the rear end portion 12 of the metallic shell 50 and the separator 200 for their protection. That opening end 46 of the tubular housing 45 which is located toward the forward side CL1 is engaged with the outer circumference of the rear-end engagement portion 57 of the metallic shell 50, is crimped from radially outside, and is full-circle laser-welded to the rear-end engagement portion 57. By this procedure, the tubular housing 45 is attached to the metallic shell 50.

A tubular metal holding member 70 is provided in a gap between the tubular housing 45 and the separator 200. The metal holding member 70 has a support portion 71 formed by bending its rear end inward. The support portion 71 butts against a collar portion 201 provided at a rear-end outer circumference of the separator 200. Thus, the metal holding member 70 supports the separator 200. In a state in which the metal holding member 70 supports the separator 200, the outer circumferential surface of the tubular housing 45 is crimped at a position corresponding to the metal holding member 70, whereby the metal holding member 70 which supports the separator 200 is fixed to the tubular housing 45.

Furthermore, a grommet 75 is provided on the rear side of the separator 200. The grommet 75 closes the tubular housing 45 at its rear end. The grommet 75 has five lead wire insertion holes 76 (FIG. 1 shows one of them) for allowing the five lead wires 78 to extend outward therethrough.

Figure 2:
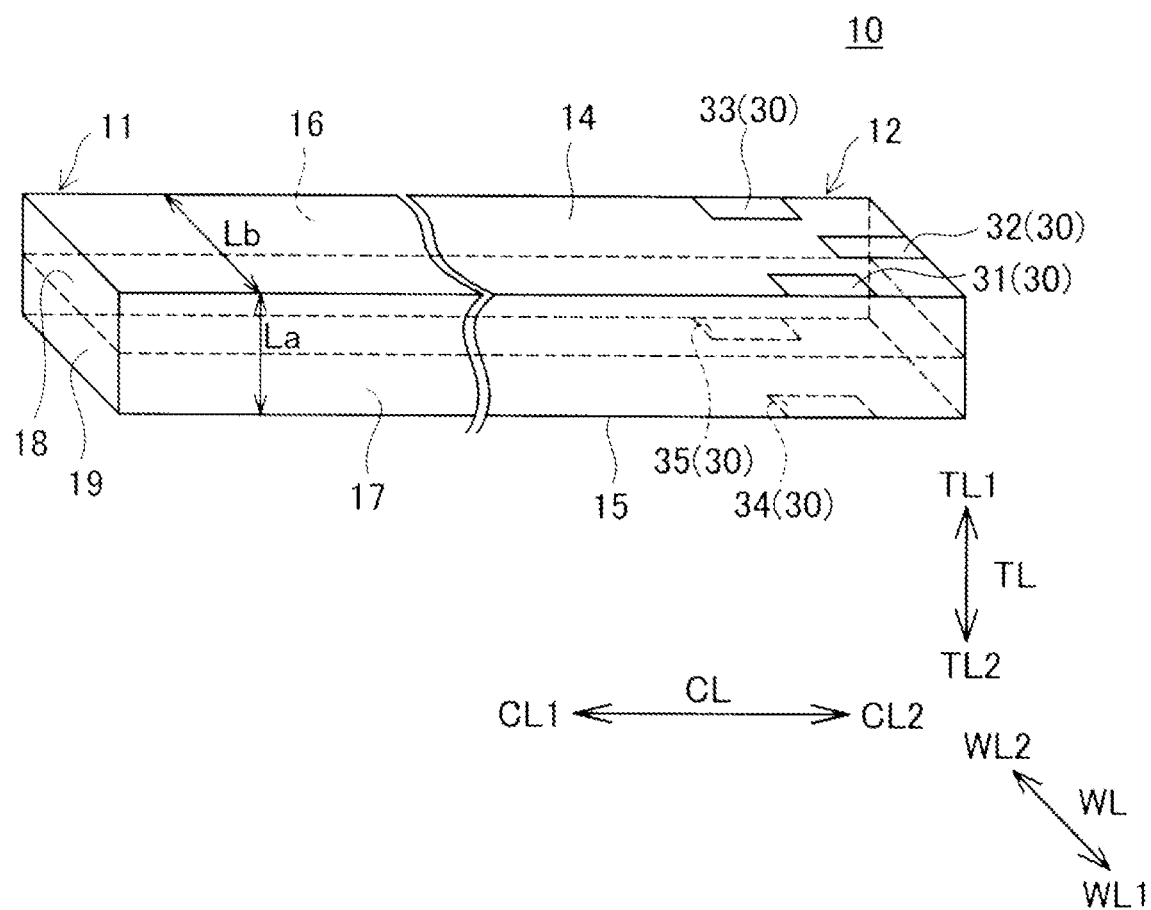
FIG. 2 View for explaining the constitution of a detection element.

FIG. 2 is a view for explaining the constitution of the detection element 10. FIG. 2 schematically shows the detection element 10. The detection element 10 has a first main surface 14 and a second main surface 15 which constitute a portion of the surface thereof, and a first side surface 16 and a second side surface 17 which constitute another portion of the surface. The first main surface 14 and the second main surface 15 extend along the axial direction CL. The first main surface 14 and the second main surface 15 face opposite each other. The first side surface 16 and the second side surface 17 extend along the axial direction CL. The first side surface 16 and the second side surface 17 face opposite each other. The first main surface 14 and the second main surface 15 are greater in surface area than the first side surface 16 and the second side surface 17.

A direction in which the first main surface 14 and the second main surface 15 face opposite each other is defined as a thickness direction TL of the detection element 10, and a direction in which the first side surface 16 and the second side surface 17 face opposite each other is defined as a width direction WL of the detection element 10. The thickness direction TL directed from the second main surface 15 toward the first main surface 14 is defined as a first thickness direction TL1, and the thickness direction TL directed from the first main surface 14 toward the second main surface 15 is defined as a second thickness direction TL2. The width direction WL directed from the first side surface 16 toward the second side surface 17 is defined as a first width direction WL1, and the width direction WL directed from the second side surface 17 toward the first side surface 16 is defined as a second width direction WL2. As shown in FIG. 2, La represents the length of the detection element 10 along the thickness direction TL, and Lb represents the length of the detection element 10 along the width direction WL. The detection element 10 satisfies the relational expression "Lb>La."

The detection element 10 is configured such that an element 18 and a heater 19 are laminated together in the thickness direction TL. The element 18 and the heater 19 each have a plate-like form extending along the axial direction CL. As viewed from the axial direction CL, the detection element 10 has a rectangular shape whose longitudinal direction coincides with the width direction WL and which has four edges substantially perpendicular to each other. The detection element 10 used in a full range air/fuel ratio sensor is publicly known, but its schematic configuration will be described below.

The element 18 is composed of an oxygen concentration cell element configured such that porous electrodes are formed on opposite sides of a solid electrolyte substrate; an oxygen pump element configured such that porous electrodes are formed on opposite sides of a solid electrolyte substrate; and a spacer sandwiched between these two elements to thereby form a hollow measuring gas chamber. The solid electrolyte substrates are formed of zirconia which contains yttria as a stabilizer in solid solution. The porous electrodes are formed primarily of Pt. The spacer used to form the measuring gas chamber is formed primarily of alumina. One porous electrode of the oxygen concentration cell element and one porous electrode of the oxygen pump element are disposed in such a manner as to be exposed to the interior of the hollow measuring gas chamber. The measuring gas chamber is formed in the forward end portion 11 of the detection element 10, and the portion where the measuring gas chamber is formed corresponds to the detection portion. The heater 19 is formed such that a heat-generating resistor pattern formed primarily of Pt is sandwiched between insulating substrates formed primarily of alumina.

Three electrode terminals 31, 32, and 33 are disposed on that portion of the first main surface 14 of the detection element 10 which is located toward the rear side CL2. Two electrode terminals 34 and 35 are disposed on that portion of the second main surface 15 of the detection element 10 which is located toward the rear side CL2. The electrode terminal 31 may also be called the "first electrode terminal 31," the electrode terminal 32 as the "second electrode terminal 32," the electrode terminal 33 as the "third electrode terminal 33," the electrode terminal 34 as the "fourth electrode terminal 34," and the electrode terminal 35 as the "fifth electrode terminal 35." When the first to fifth electrode terminals 31 to 35 are to be generically referred to, the term "electrode terminals 30" is used.

In the present embodiment, the first to third electrode terminals 31 to 33 are disposed along the width direction WL. That is, the first to third electrode terminals 31 to 33 are disposed at positions shifted from one another in the width direction WL. The second electrode terminal 32 is disposed at a position located further toward the rear side CL2 than the first and third electrode terminals 31 and 33. The fourth and fifth electrode terminals 34 and 35 are disposed along the width direction WL. That is, the fourth and fifth electrode terminals 34 and 35 are disposed at positions shifted from each other in the width direction WL.

The first to third electrode terminals 31 to 33 are formed on the element 18, and one of the first to third electrode terminals 31 to 33 is electrically connected, in common, to one porous electrode of the oxygen concentration cell element exposed to the interior of the measuring gas chamber and to one porous electrode of the oxygen pump element. The remaining two of the first to third electrode terminals 31, 32, and 33 are electrically connected to the other porous electrode of the oxygen concentration cell element and to the other porous electrode of the oxygen pump cell, respectively. The fourth and fifth electrode terminals 34 and 35 are formed on the heater 19 and are connected to opposite ends, respectively, of the heat-generating resistor pattern through vias (not shown) extending through the heater 19 in the thickness direction.

A-2. Detailed Constitution of Terminal Members

Figure 3:
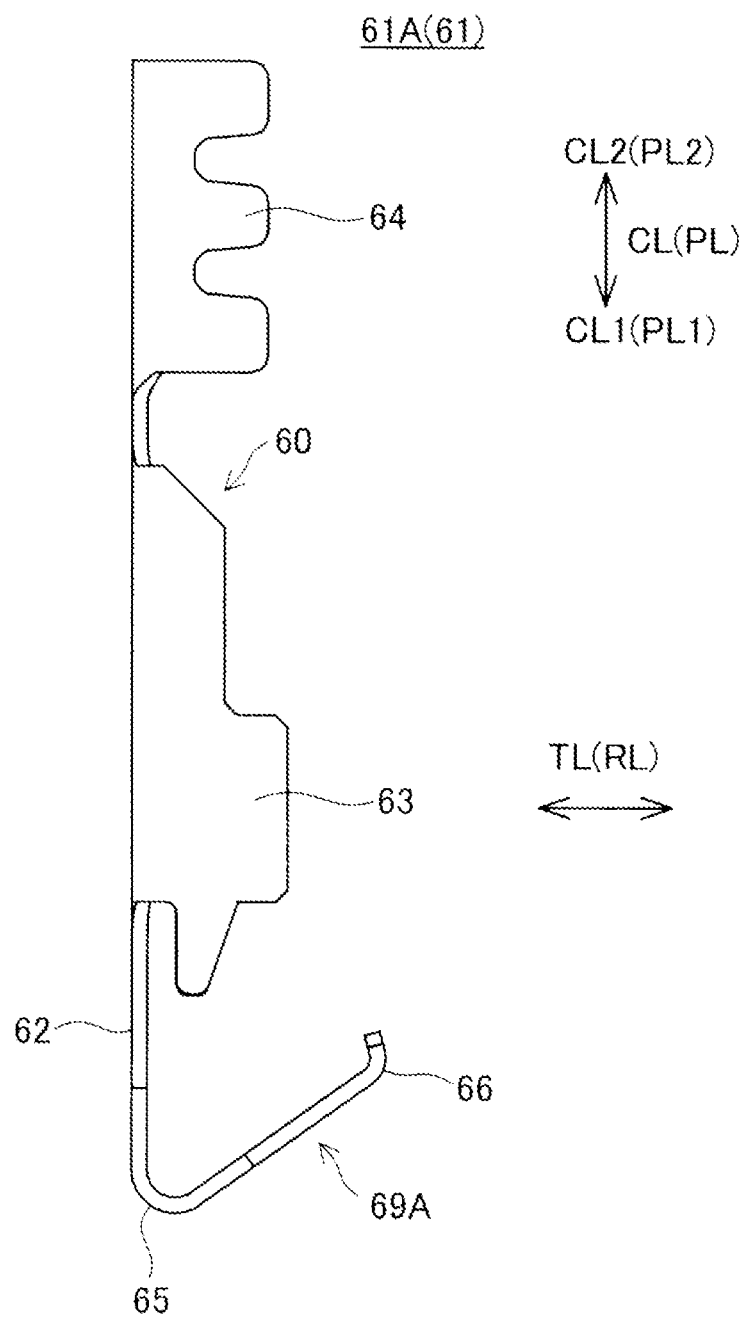
FIG. 3 Side view of a first-type terminal member.
Figure 4:
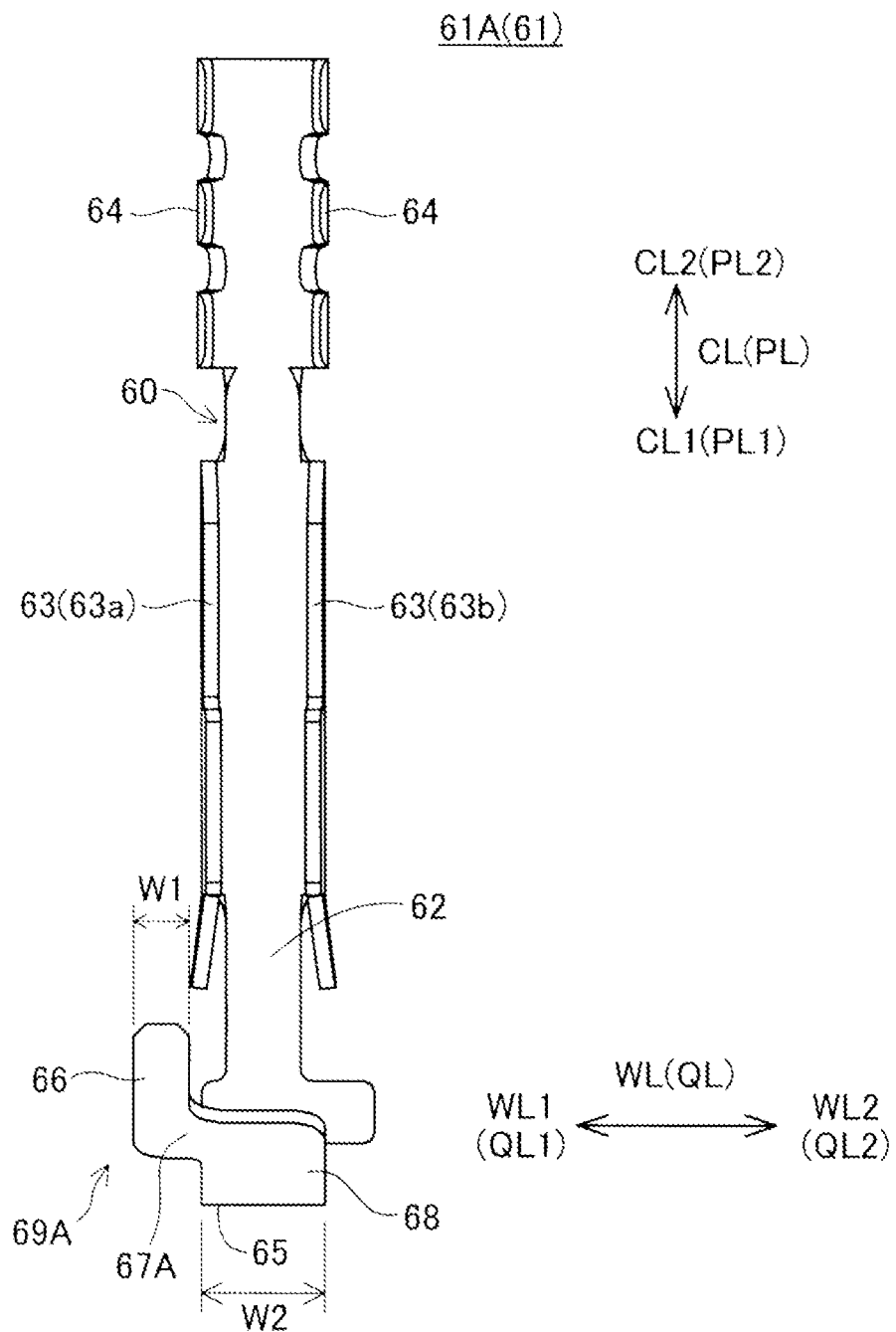
FIG. 4 Front view of the first-type terminal member.
Figure 5:
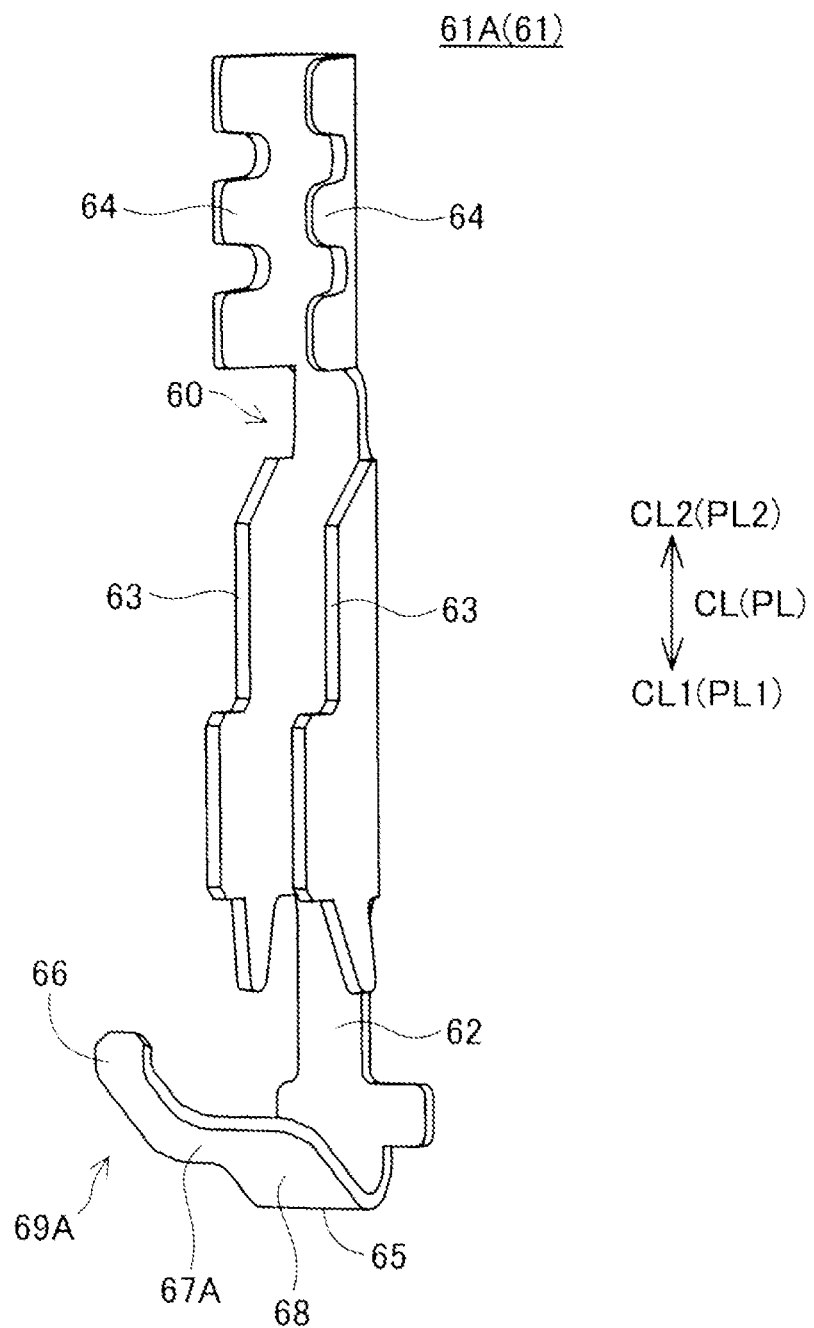
FIG. 5 Perspective view of the first-type terminal member.
Figure 6:
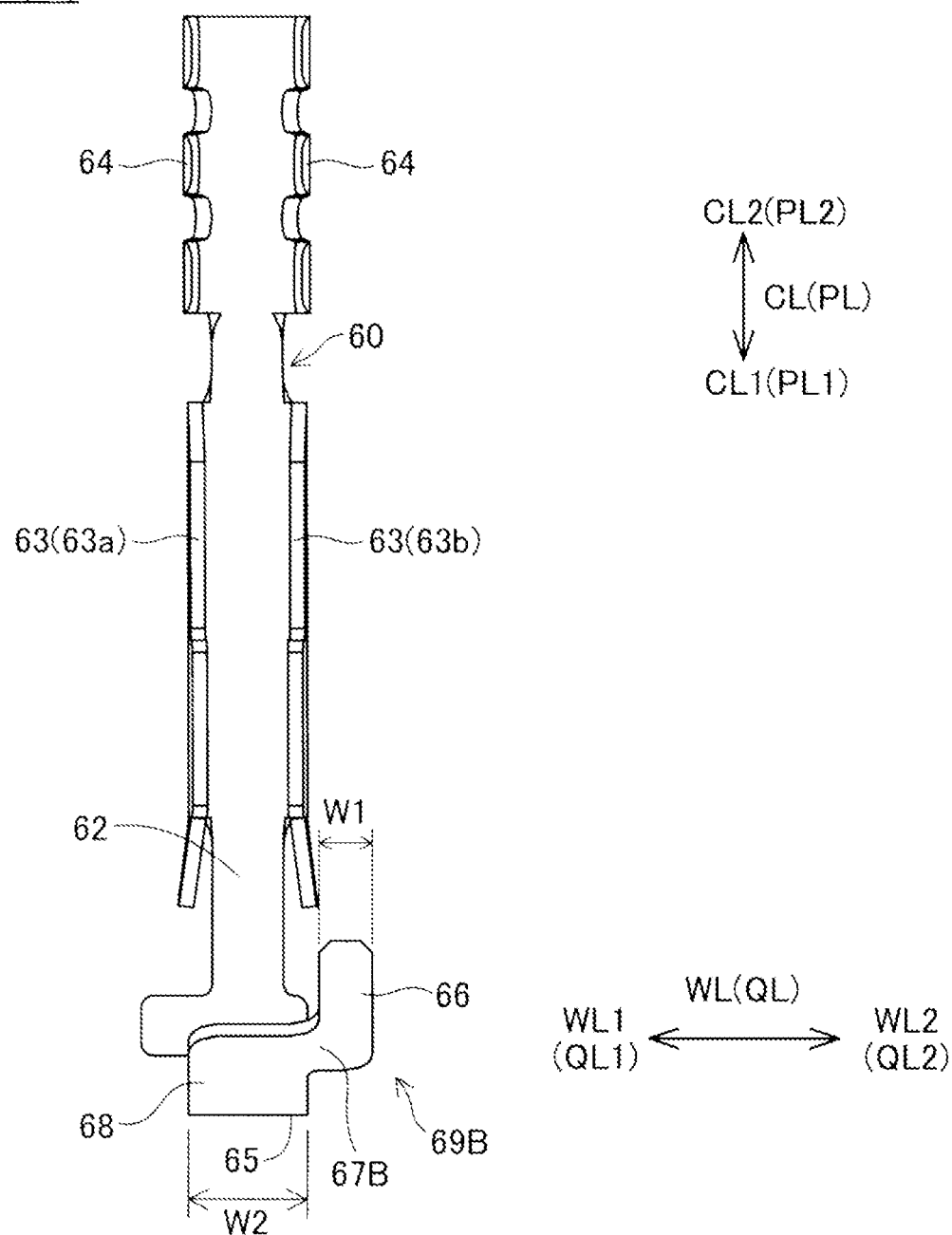
FIG. 6 Front view of a second-type terminal member.
Figure 7:
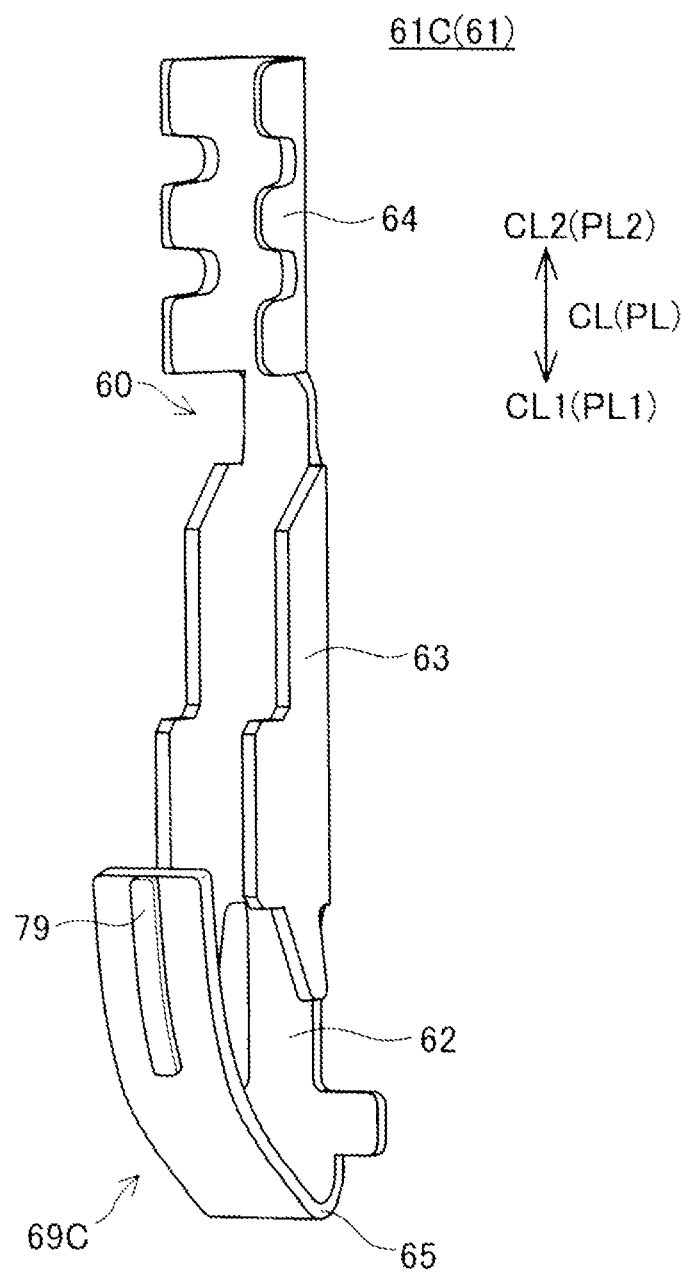
FIG. 7 Perspective view of a third-type terminal member.

FIG. 3 is a side view of the first-type terminal member 61A. FIG. 4 is a front view of the first-type terminal member 61A. FIG. 5 is a perspective view of the first-type terminal member 61A. FIG. 6 is a front view of the second-type terminal member 61B. FIG. 7 is a perspective view of the third-type terminal member 61C. In the present specification, when the first to third terminal members 61A to 61C are to be generically referred to without being distinguished from one another, the term "terminal members 61" is used.

The first-type terminal member 61A is used with the third electrode terminal 33 and the fourth electrode terminal 34; the second-type terminal member 61B is used with the first electrode terminal 31 and the fifth electrode terminal 35; and the third-type terminal member 61C is used with the second electrode terminal 32.

The terminal members 61 are formed of metal such as INCONEL or stainless steel. Preferably, material used to form the terminal members 61 can maintain spring elasticity even when repeatedly exposed to high temperature.

As shown in FIGS. 3 to 5, the first-type terminal member 61A includes a frame body portion 60, a folded portion 65, and the element contact portion 69A. The frame body portion 60 has an elongated shape extending along the axial direction CL. In the first-type terminal member 61A, a direction in which the frame body portion 60 extends is defined as a longitudinal direction PL. When the terminal member 61A is incorporated into the gas sensor 1, the longitudinal direction PL and the axial direction CL coincide with each other.

As shown in FIGS. 4 and 5, the frame body portion 60 has a body 62, a connection portion 64, and a pair of positioning portions 63. The body 62 is a plate-like member extending along the axial direction CL. The connection portion 64 is formed at the rear side CL2 of the frame body portion 60. In a state in which the corresponding lead wire 78 is inserted into the connection portion 64, the connection portion 64 is crimped inward, thereby holding the lead wire 78. By this procedure, the lead wire 78 and the first-type terminal member 61A are electrically connected to each other. The paired positioning portions 63 are plate-like members protruding from opposite sides, with respect to the width direction WL, of the body 62. By means of the positioning portions 63 being at least partially accommodated in the separator 200, movement of the terminal member 61A in the width direction WL is restricted. The paired positioning portions 63 form the sides, with respect to the width direction WL, of the frame body portion 60. In a state in which the terminal member 61A is incorporated into the gas sensor 1, one of the paired positioning portions 63 which is located inward with respect to the width direction WL of the detection element 10 is referred to as a positioning portion 63a, and the other one located outward with respect to the width direction WL as a positioning portion 63b.

As shown in FIG. 3, the folded portion 65 connects the frame body portion 60 and the element contact portion 69A. The folded portion 65 is folded such that the element contact portion 69A extends toward the rear side CL2. That is, the folded portion 65 is a portion of the terminal member 61A located furthest toward the forward side CL1.

As shown in FIG. 3, the element contact portion 69A faces the frame body portion 60. As shown in FIGS. 4 and 5, the element contact portion 69A has a base portion 68, a contact portion 66, and a turning portion 67A. The base portion 68 is connected to the folded portion 65. The contact portion 66 actually comes into contact with the electrode terminal 30. The turning portion 67A is located between the contact portion 66 and the folded portion 65 and between the contact portion 66 and the base portion 68. A side of the element contact portion 69A toward the folded portion 65 is referred to as a contact-portion forward side PL1, and a side toward the turning portion 67A as a contact-portion rear side PL2. In the terminal member 61A, a direction which is orthogonal to the axial direction CL and in which the frame body portion 60 and the element contact portion 69A face each other is referred to as a thickness direction RL of the terminal member 61A. When the terminal member 61A is incorporated into the gas sensor 1, the thickness direction RL and the thickness direction TL coincide with each other. A direction orthogonal to the axial direction CL and to the thickness direction RL is referred to as a width direction QL of the terminal member 61A. When the terminal member 61A is incorporated into the gas sensor 1, the width direction QL and the width direction WL coincide with each other. The width direction QL of the terminal member 61A which corresponds to the first width direction WL1 of the detection element 10 is referred to as a first width direction QL1, and a direction corresponding to the second width direction WL2 of the detection element 10 as a second width direction QL2.

The contact portion 66 moves through elastic deformation with the folded portion 65 serving as a fulcrum. A width W1 of the contact portion 66 is narrower than a width W2 of the folded portion 65. The contact portion 66 may assume the form of a protrusion provided on that surface of the element contact portion 69A which faces the detection element 10. An example of the protrusion is a protrusion 79 of the third-type terminal member 61C (FIG. 7), which will be described later. In this case, the width W1 of the contact portion 66 means the width of the protrusion.

As shown in FIG. 4, the turning portion 67A turns toward the width direction WL. More specifically, the turning portion 67A turns toward the first width direction WL1 from the base portion 68 to the contact portion 66. Thus, the contact portion 66 is disposed at a position shifted in the width direction WL from the folded portion 65. The terminal member 61A is incorporated into the gas sensor 1 such that the turning portion 67A turns inward with respect to the width direction WL. That is, the turning portion 67A is located inward with respect to the width direction WL of the detection element 10 in the course from the base portion 68 to the contact portion 66.

As shown in FIG. 6, the second-type terminal member 61B assumes the form of a mirror image of the first-type terminal member 61A shown in FIG. 4. That is, a turning portion 67B of an element contact portion 69B turns toward an opposite direction of the first-type terminal member 61A. Other constitutional features are similar to those of the first-type terminal member 61A. Thus, the similar constitutional features are denoted by the same reference numerals as those of the first-type terminal member 61A, and repeated description thereof is omitted. The turning portion 67B turns toward the second width direction WL2 in the course from the base portion 68 to the contact portion 66.

As shown in FIG. 7, the third-type terminal member 61C differs from the first-type terminal member 61A in the constitution of an element contact portion 69C. Other constitutional features are similar to those of the first-type terminal member 61A; thus, the similar constitutional features are denoted by the same reference numerals as those of the first-type terminal member 61A, and repeated description thereof is omitted. The element contact portion 69C does not have the turning portion 67A (68B). Also, the element contact portion 69C has the protrusion 79. The protrusion 79 actually comes into contact with the second electrode terminal 32.

A-3. Detailed Constitution of Separator 200

Figure 8:
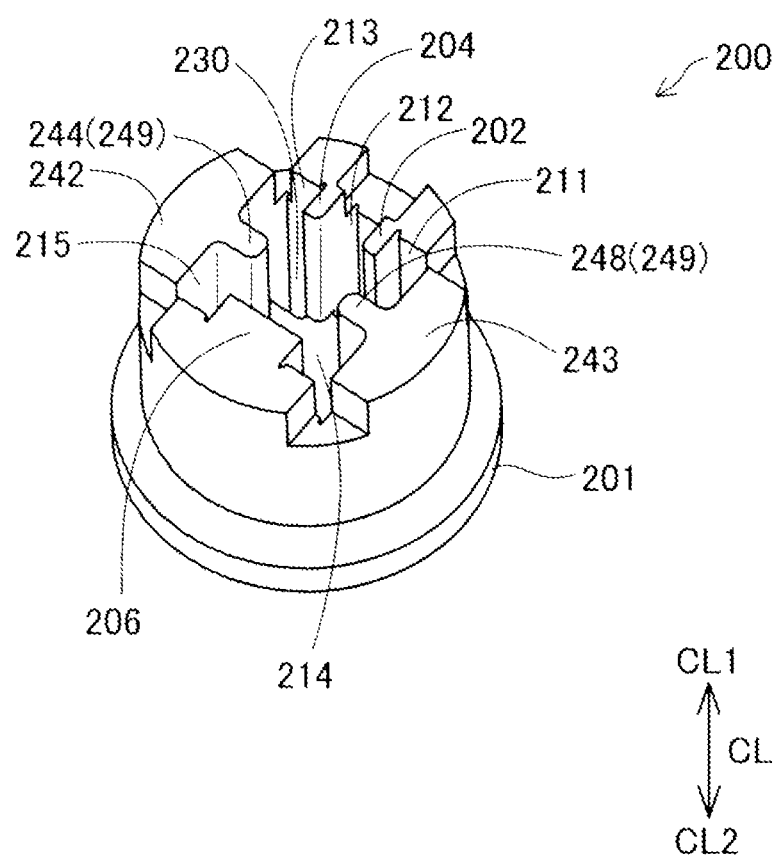
FIG. 8 Perspective view of a separator.
Figure 9:
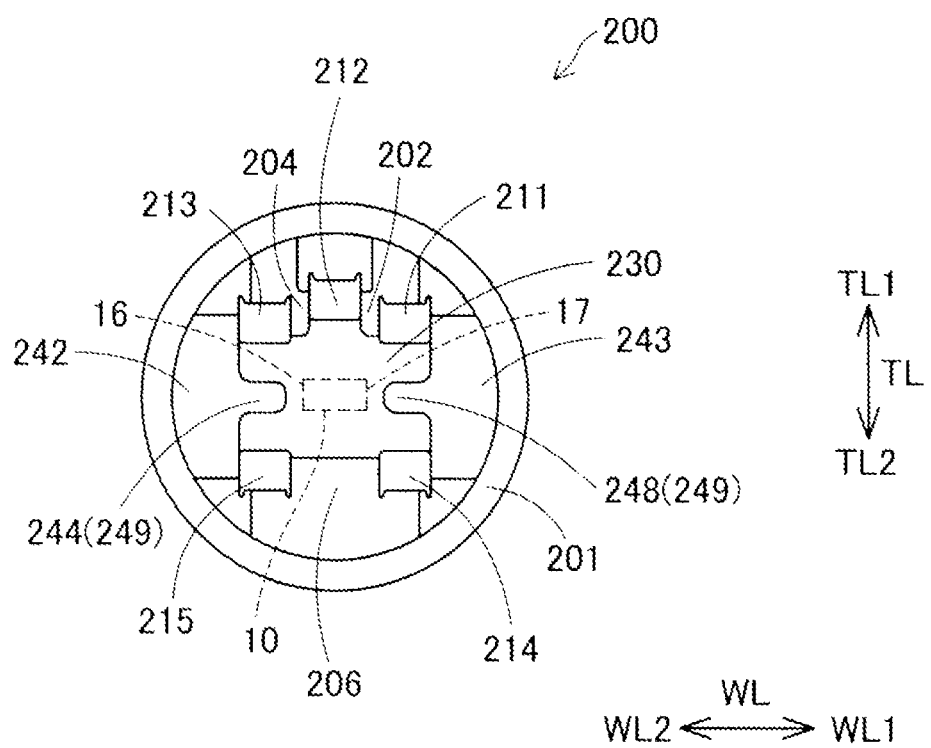
FIG. 9 View of the separator as viewed from the forward side with respect to an axial direction CL.

FIG. 8 is a perspective view of the separator 200. FIG. 9 is a view of the separator 200 as viewed from the forward side CL1 with respect to the axial direction CL. For easy understanding, in FIG. 9, the detection element 10 is represented by the dotted line. As shown in FIGS. 8 and 9, the separator 200 has an accommodation chamber 230 which is a through hole extending therethrough in the axial direction CL from its forward end to its substantial center. The accommodation chamber 230 accommodates those portions (may be referred to as "terminal forward end portions") of the terminal members 61 which are located on the forward side CL1, and the rear end portion 12 of the detection element 10 on which the electrode terminals 30 are disposed.

The accommodation chamber 230 has, at an outer circumferential portion of the separator 200, first to fifth terminal accommodation chambers 211 to 215 which are through holes extending in the axial direction CL through the separator 200 from the forward end to the rear end of the separator 200. The separator 200 has three partition walls 202, 204, and 206 and two side partition walls 244 and 248 in the accommodation chamber 230. The first terminal accommodation chamber 211 and the fifth terminal accommodation chamber 215 each accommodate the second-type terminal members 61B. The third terminal accommodation chamber 213 and the fourth terminal accommodation chamber 214 each accommodate the first-type terminal member 61A. The second terminal accommodation chamber 212 accommodates the third-type terminal member 61C. The first to fifth terminal chambers 211 to 215 each accommodate that portion of the frame body portion 60 which is located toward the forward side CL1.

The first partition wall 202 is disposed between the first terminal accommodation chamber 211 and the second terminal accommodation chamber 212. The second partition wall 204 is disposed between the second terminal accommodation chamber 212 and the third terminal accommodation chamber 213. The third partition wall 206 is disposed between the fourth terminal accommodation chamber 214 and the fifth terminal accommodation chamber 215. The first to third partition walls 202, 204, and 206 are members of the separator 200 and are formed of electrically insulating ceramic. The first to third partition walls 202, 204, and 206 extend along the axial direction CL in the accommodation chamber 230.

As shown in FIG. 9, the first side partition wall 244 faces the first side surface 16 of the detection element 10. The first side partition wall 244 protrudes toward the first side surface 16 of the detection element 10 from a peripheral wall 242 which partially constitutes the outer circumference of the separator 200. The first side partition wall 244 is located between the third terminal accommodation chamber 213 and the fifth terminal accommodation chamber 215. That is, the first side partition wall 244 is located between the paired terminal members 61A and 61B which are disposed in a facing manner on opposite sides of the detection element 10 with respect to the thickness direction TL.

As shown in FIG. 9, the second side partition wall 248 faces the second side surface 17 of the detection element 10. The second side partition wall 248 protrudes toward the second side surface 17 of the detection element 10 from a peripheral wall 243 which partially constitutes the outer circumference of the separator 200. The second side partition wall 248 is located between the first terminal accommodation chamber 211 and the fourth terminal accommodation chamber 214. That is, the second side partition wall 248 is located between the paired terminal members 61A and 61B which are disposed in a facing manner on opposite sides of the detection element 10 with respect to the thickness direction TL. The first and second side partition walls 244 and 248 are members of the separator 200 and are formed of electrically insulating ceramic. The first and second side partition walls 244 and 248 extend along the axial direction CL in the accommodation chamber 230. When the first and second side partition walls 244 and 248 are to be generically referred to without being distinguished from each other, the term "side partition walls 249" is used.

Figure 10:
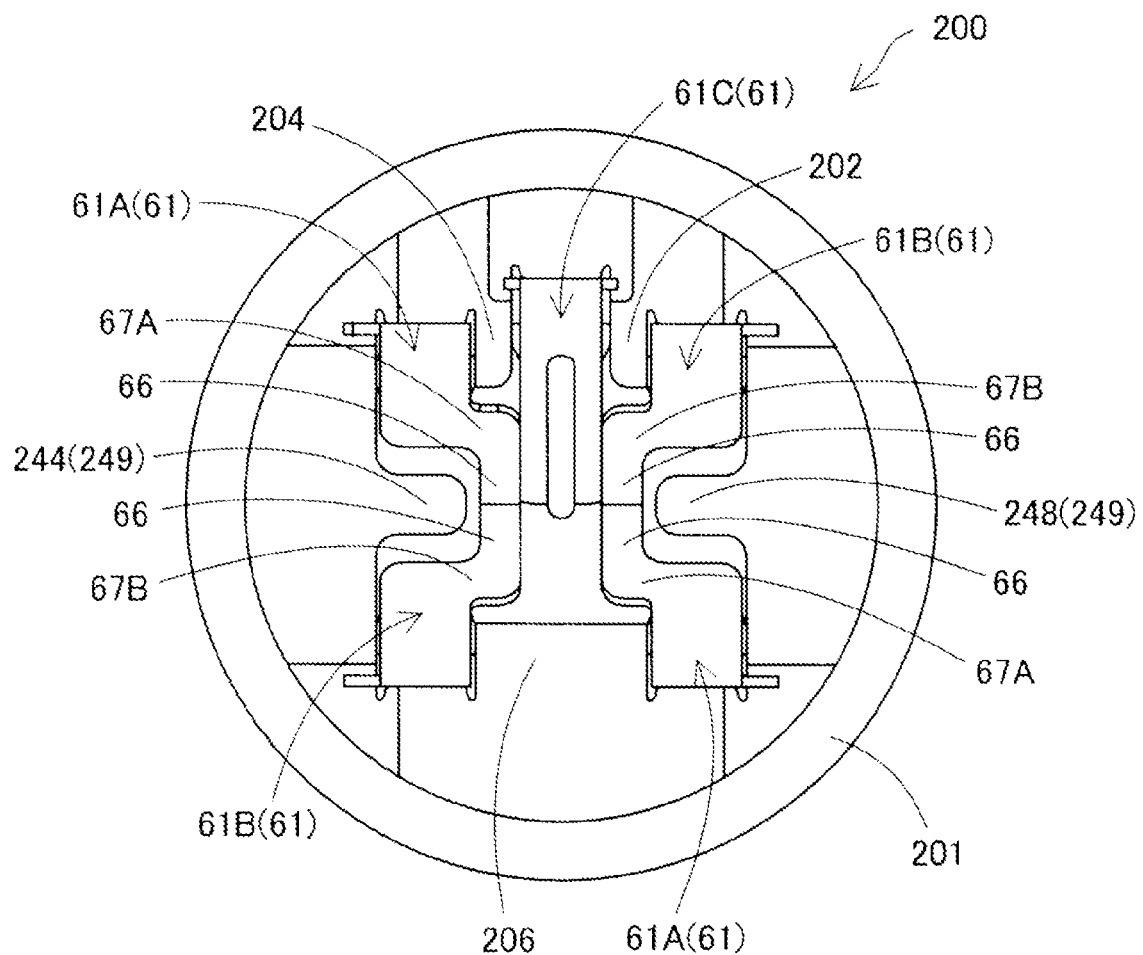
FIG. 10 View showing the separator in which the terminal members are accommodated.
Figure 10:
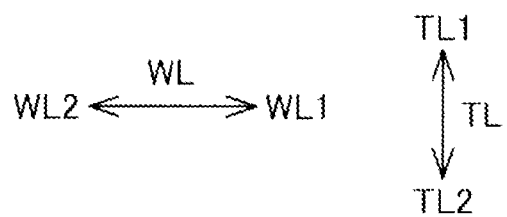
Figure 11:
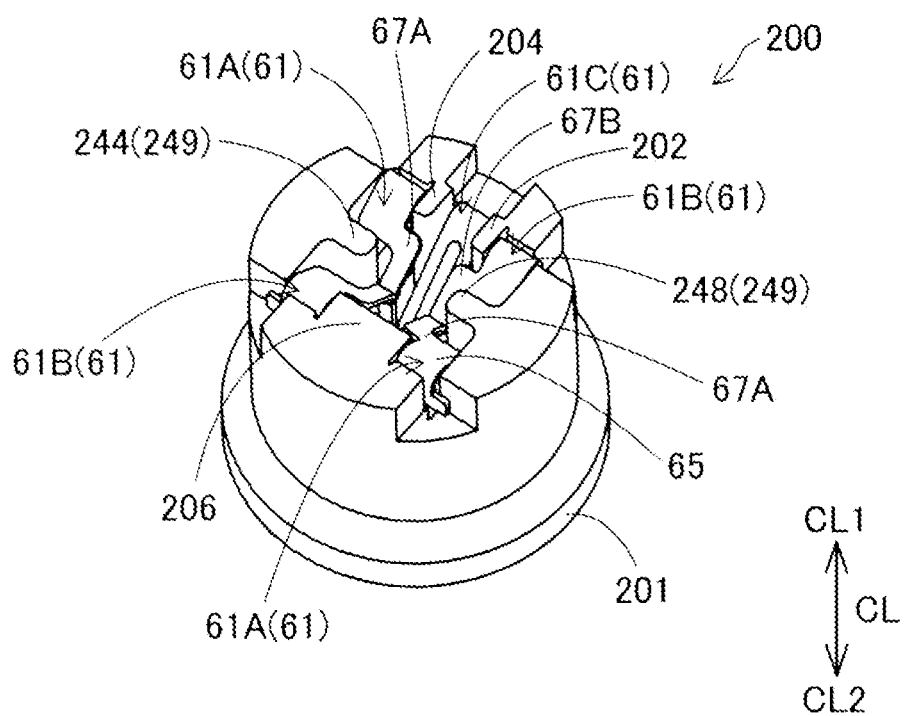
FIG. 11 Perspective view of the separator of FIG. 10.

FIG. 10 shows the separator 200 in which the terminal members 61 are accommodated. FIG. 10 is a view of the separator 200 as viewed from the forward side CL1 with respect to the axial direction CL. When the detection element 10 and the terminal members 61 are to be incorporated into the separator 200, first, as shown in FIGS. 10 and 11, the terminal members 61 are disposed in the separator 200.

Figure 12:
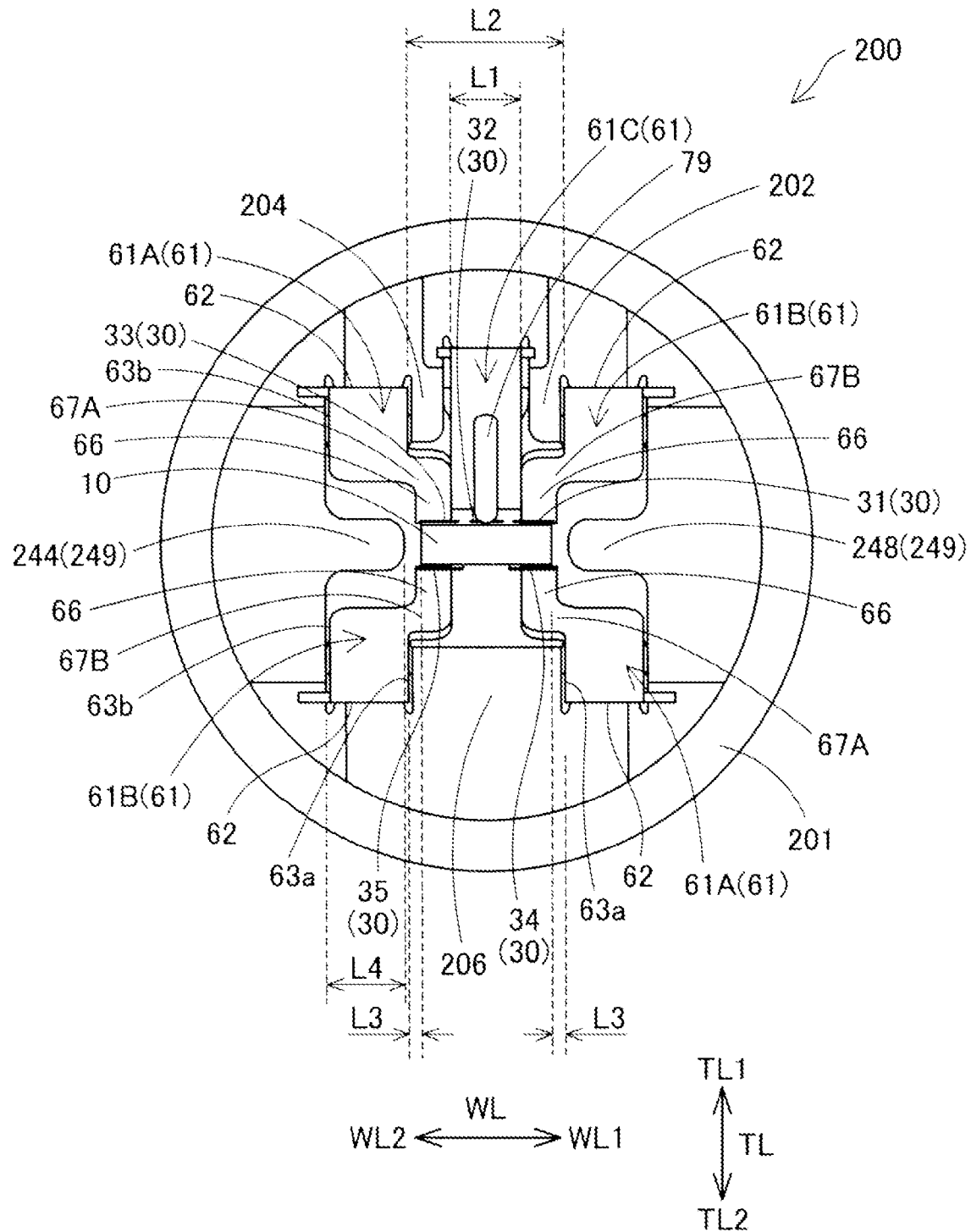
FIG. 12 view of the separator in which the terminal members and the detection element are accommodated, as viewed from the forward side with respect to the axial direction CL.

FIG. 12 is a view of the separator 200 in which the terminal members 61 and the detection element 10 are accommodated, as viewed from the forward side CL1 with respect to the axial direction CL. After the terminal members 61 are accommodated into the separator 200, the rear end portion 12 of the detection element 10 is inserted into the separator 200 toward the rear side CL2 with respect to the axial direction CL such that the electrode terminals 30 come into contact with the connection portions 66 and 79, respectively. As a result of insertion of the rear end portion 12 of the detection element 10 into the separator 200, the element contact portions 69A, 69B, and 69C (FIGS. 5 to 7) move toward the frame body portions 60 (FIGS. 5 to 7), respectively. Thus, the contact portions 66 and 79 come into elastic contact with the electrode terminals 30, respectively.

As shown in FIG. 12, in two terminal members 61A and 61B adjacent to each other along the width direction WL, the distance along the width direction WL between the contact portions 66 is defined as distance L1. Also, in the two terminal members 61A and 61B adjacent to each other along the width direction WL, the distance along the width direction WL between the frame body portions 60 is defined as distance L2. In this case, the gas sensor 1 satisfies the relational expression "distance L1<distance L2." The two terminal members 61A and 61B adjacent to each other along the width direction WL have the turning portions 67A and 67B, respectively. The partition walls 202, 204, and 206 are each disposed between the frame body portions 60 of the two terminal members 61A and 61B adjacent to each other along the width direction WL.

As shown in FIGS. 4 and 12, the frame body portions 60 of the first-type terminal member 61A and the second-type terminal member 61B are located outward of the detection element 10 with respect to the width direction WL. That is, of the side surfaces of the frame body portions 60 of the first-type terminal member 61A and the second-type terminal member 61B, the inner side surfaces (positioning portions 63a) located inward with respect to the width direction WL are located length L3 outward of the corresponding side surfaces of the detection element 10 with respect to the width direction WL.

As shown in FIGS. 5, 6, and 12, the side partition wall 249 is located between the paired frame body portions 60 which are disposed in a facing manner on opposite sides of the detection element 10 with respect to the thickness direction TL. Also, the first side partition wall 244 is located inward, with respect to the width direction WL, of those outer side surfaces 63b of the paired frame body portions 60 which are located outward with respect to the width direction WL. Specifically, the first side partition wall 244 is located distance L4 inward of the outer side surfaces 63b of the frame body portions 60 with respect to the width direction WL. The second side partition wall 248 also has similar relational features.

The first-type terminal member 61A and the second-type terminal member 61B correspond to the "terminal members" appearing in the section "Means for Solving The Problems." As shown in FIG. 12, the first-type terminal member 61A and the second-type terminal member 61B adjacent to each other along the width direction WL correspond to "two terminal members adjacent to each other along the width direction" appearing in the section "Means for Solving the Problems." As shown in FIG. 12, the frame body portions 60 of the first-type terminal member 61A and the second-type terminal member 61B which face each other in the thickness direction TL correspond to "a pair of the frame body portions" appearing in the section "Means for Solving The Problems." Also, the first side partition wall 244 and the second side partition wall 248 correspond to the "side partition wall" appearing in the section "Means for Solving The Problems."

A-4. Effects

According to the embodiment described above, the first-type terminal member 61A and the second-type terminal member 61B adjacent to each other along the width direction WL have the turning portions 67A and 67B, respectively (FIGS. 4 and 6). Thus, the gas sensor 1 satisfies the relational expression "distance L2>distance L1" (FIG. 12). Therefore, while spacing (distance L2) is provided between the frame body portions 60 of the two terminal members 61A and 61B adjacent to each other along the width direction WL, good contact can be established between the element contact portions 69A and 69B of the first-type and second-type terminal members 61A and 61B and the corresponding electrode terminals 30 of the detection element 10. By means of spacing being provided between the frame body portions 60 of the two terminal members 61A and 61B adjacent to each other along the width direction WL, there can be reduced the possibility of electrical connection between the two terminal members 61A and 61B adjacent to each other along the width direction WL, so that the detection accuracy of the gas sensor 1 can be improved. As mentioned above, according to the present embodiment, for example, even when the detection element 10 is reduced in size along the width direction WL, while good contact is established between the electrode terminals 30 and the corresponding terminal members 61A and 61B, there can be reduced the possibility of electrical connection between the frame body portions 60 of the terminal members 61A and 61B adjacent to each other along the width direction WL.

Particularly, in the present embodiment, of the side surfaces of the frame body portions 60 of the first-type terminal member 61A and the second-type terminal member 61B, the inner side surfaces (positioning portions 63a) located inward with respect to the width direction WL are located outward of the detection element 10 with respect to the width direction WL. Thus, sufficient spacing can be provided between the frame body portions 60 adjacent to each other with respect to the width direction WL. Therefore, there can be further reduced the possibility of electrical connection between the terminal members 61A and 61B adjacent to each other along the width direction WL, so that the detection accuracy of the gas sensor 1 can be further improved.

Also, in the embodiment described above, the electrically insulating partition walls 202, 204, and 206 are each disposed between the frame body portions 60 of the two terminal members 61A and 61B adjacent to each other along the width direction WL (FIG. 12). Thus, there can be further reduced the possibility of electrical connection between the two frame body portions 60 adjacent to each other along the width direction WL, so that the detection accuracy of the gas sensor 1 can be further improved.

Also, in the embodiment described above, in the first-type terminal member 61A and the second-type terminal member 61B, the width W1 of the contact portion 66 is narrower than the width W2 of the folded portion 65 (FIGS. 4 and 6). Thus, while deterioration in rigidity of the folded portion 65 is restrained, elastic force (contact pressure) which the contact portion 66 applies to the electrode terminal 30 can be increased. Therefore, there can be reduced the possibility of breaking the electrical connection between the first-type and second-type terminal members 61A and 61B and the corresponding electrode terminals 30.

Also, in the embodiment described above, the separator 200 has the first side partition wall 244 which faces the first side surface 16 of the detection element 10. The first side partition wall 244 is located distance L4 inward, with respect to the width direction WL, of the outer side surfaces 63b of the paired frame body portions 60 which are disposed in a facing manner on opposite sides of the detection element 10 with respect to the thickness direction TL (FIG. 12). The second side partition wall 248 which faces the first side partition wall 244 with respect to the width direction WL with the detection element 10 located therebetween also has similar relational features. Thus, spacing along the width direction WL between the first side partition wall 244 and the detection element 10 can be reduced. Also, spacing along the width direction WL between the second side partition wall 248 and the detection element 10 can be reduced. Therefore, even when the detection element 10 receives a force in the width direction WL due to vibration of the sensor 1, or the like, the first and second side partition walls 244 and 248 impinge against the detection element 10, thereby restricting movement of the detection element 10 along the width direction WL. Thus, positional misalignment of the detection element 10 within the gas sensor 1 can be restrained. Also, since the terminal members 61 are disposed respectively between the first side partition wall 244 and each of the partition walls 204 and 206 and between the second side partition wall 248 and each of the partition walls 202 and 206, even when the terminal members 61 receives a force along the width direction WL, the terminal members 61 impinge against the side partition walls 244 and 248 and the partition walls 202, 204, and 206, whereby movement of the terminal members 61 along the width direction WL can be restricted. Therefore, in attachment of the terminal members 61 to the separator 200, positional misalignment of the terminal members 61 can be restrained.

B. Modifications

B-1. First Modification

In the embodiment described above, the first-type and second-type terminal members 61A and 61B have the turning portion 67A and 67B, respectively; however, at least the first-type terminal member 61A has the turning portion 67A. That is, at least either the first-type terminal member 61A or the second-type terminal member 61B may have the corresponding turning portion 67A or 67B. Even in such a case, the gas sensor 1 satisfies the relational expression "distance L2>distance L1;" thus, as in the case of the embodiment described above, the detection accuracy of the gas sensor 1 can be improved.

B-2. Second Modification

In the embodiment described above, the detection element 10 has five electrode terminals 31 to 35; however, the number of the electrode terminals is not limited thereto. For example, the detection element 10 may have four electrode terminals 31, 33, 34, and 35 without having the second electrode terminal 32.

B-3. Third Modification

The first-type and second-type terminal members 61A and 61B are not limited in shape to the embodiment described above, but may have other shapes so long as the turning portions 67A and 67B are provided. For example, portions of the first-type and second-type terminal members 61A and 61B may be twisted along a plane orthogonal to the axial direction CL.

The present invention is not limited to the above-mentioned embodiment and modifications, but may be embodied in various other forms without departing from the spirit of the invention. For example, in order to solve, partially or entirely, the above-mentioned problems or yield, partially or entirely, the above-mentioned effects, technical features of the modes described in the section "Summary of the Invention" and technical features of the modifications can be replaced or combined as appropriate. Also, the technical feature(s) may be eliminated as appropriate unless the present specification mentions that the technical feature(s) is mandatory.

DESCRIPTION OF REFERENCE NUMERALS

1: gas sensor
8: protector
9: detection portion protection layer
10: detection element
11: forward end portion
12: rear end portion
13: central portion
14: first main surface
15: second main surface
16: first side surface
17: second side surface
18: element
20: cup
21: ceramic ring
22: talc ring
23: forward-end peripheral portion
25: opening
26: talc ring
27: sleeve
28: shoulder portion
29: packing
30: electrode terminal
31: first electrode terminal
32: second electrode terminal
33: third electrode terminal
34: fourth electrode terminal
35: fifth electrode terminal
45: tubular housing
46: opening end
50: metallic shell
51: externally threaded portion
52: tool engagement portion
53: crimped portion
54: stepped portion
55: gasket
56: forward-end engagement portion
57: rear-end engagement portion
60: frame body portion
61: terminal member
61A: first-type terminal member
61B: second-type terminal member
61C: third-type terminal member
62: body
63: positioning portion
63a: positioning portion (inner side surface)
63b: positioning portion (outer side surface)
64: connection portion
65: folded portion
66: contact portion
67A, 67B: turning portion
68: base portion
69, 69A to 69C: element contact portion
70: metal holding member
71: support portion
75: grommet
76: lead wire insertion hole
78: lead wire
79: protrusion
80: outer protector
85: outer introduction hole
90: inner protector
95: inner introduction hole
96: drain hole
97: discharge hole
200: separator
201: collar portion
202: first partition wall
204: second partition wall
206: third partition wall
211: first terminal accommodation chamber
212: second terminal accommodation chamber
213: third terminal accommodation chamber
214: fourth terminal accommodation chamber
215: fifth terminal accommodation chamber
230: accommodation chamber
242: peripheral wall
243: peripheral wall
244: first side partition
248: second side partition wall
CL1: forward side
W1: width
L1: distance
W2: width
L2: distance
L4: distance
PL: longitudinal direction
QL: width direction
IL: thickness direction
WL: width direction
CL: axial direction
PL1: contact-portion forward side QL1: first width direction
TL1: first thickness direction
WL1: first width direction
WL2: second width direction
TL2: second thickness direction
CL2: rear side
PL2: contact-portion rear side
QL2: second width direction

The invention claimed is:

1. A sensor comprising:
a plate-like detection element extending along an axial direction and having a first main surface and a second main surface which face opposite each other and constitute a portion of a surface of the detection element, a first side surface and a second side surface which face opposite each other, extend along the axial direction, and constitute a portion of the surface of the detection element, and a plurality of electrode terminals disposed on at least one of the first and second main surfaces;
a plurality of terminal members provided in correspondence with the plurality of electrode terminals and electrically connected to the corresponding electrode terminals, each of the terminal members comprising an elongated frame body portion extending along the axial direction, an element contact portion in elastic contact with the corresponding electrode terminal, and a folded portion connecting the frame body portion and the element contact portion, the folded portion connecting the frame body portion and the element contact portion forming an acute angle; and
a separator surrounding the element contact portions and that portion of the detection element at which the plurality of electrode terminals are disposed,
wherein, with a direction in which the first main surface and the second main surface face opposite each other being defined as a thickness direction of the detection element, and a direction in which the first side surface and the second side surface face opposite each other being defined as a width direction of the detection element,
two or more of the plurality of electrode terminals are disposed along the width direction,
the element contact portion of each of the plurality of terminal members has a contact portion in contact with the corresponding electrode terminal, and a turning portion which turns inward with respect to the width direction between the folded portion and the contact portion, and
in those two of the plurality of terminal members which are adjacent to each other along the width direction, a distance along the width direction between the contact portions is smaller than a distance along the width direction between the frame body portions.

2. A sensor according to claim 1, wherein
an electrically insulating partition wall is disposed between the frame body portions of the two terminal members which are adjacent to each other along the width direction.

3. A sensor according to claim 1, wherein
of side surfaces of the frame body portion, an inner side surface located inward with respect to the width direction is located outward of the detection element with respect to the width direction.

4. A sensor according to claim 1, wherein
a width of the contact portion is narrower than a width of the folded portion.

5. A sensor according to claim 1, wherein
two of a plurality of the frame body portions constitute a pair of the frame body portions disposed in a facing manner on opposite sides of the detection element with respect to the thickness direction,
an electrically insulating side partition wall is disposed between the paired frame body portions and faces the first side surface of the detection element, and
the side partition wall is located inward, with respect to the width direction, of those outer side surfaces of the paired frame body portions which are located outward with respect to the width direction.

6. A terminal member which is brought into electrical contact with an electrode terminal provided on a detection element extending along an axial direction, comprising:
an elongated frame body portion extending along the axial direction;
an element contact portion which comes into elastic contact with the electrode terminal and which faces, at least partially, the frame body portion with respect to a thickness direction orthogonal to the axial direction; and
a folded portion connecting the frame body portion and the element contact portion,
wherein, with a direction orthogonal to the axial direction and to the thickness direction being defined as a width direction of the terminal member, the element contact portion has a contact portion which comes into contact with the electrode terminal, and a turning portion which turns toward the width direction between the folded portion and the contact portion.

7. A terminal member according to claim 6, wherein
a width of the contact portion is narrower than a width of the folded portion.

* * * * *